(12) United States Patent
Alexis

(10) Patent No.: US 6,343,258 B1
(45) Date of Patent: Jan. 29, 2002

(54) METHOD FOR TESTING FOR READINESS FOR HARVESTING OF TRIBULUS TERRESTRIS L. HAVING HIGH STEROIDAL SAPONIN CONTENT

(76) Inventor: Brian Alexis, 1250 Chelsea Ave, #D, Santa Monica, CA (US) 90404

(*) Notice: Subject to any disclaimer, the term of this patent is extended or adjusted under 35 U.S.C. 154(b) by 0 days.

(21) Appl. No.: 09/373,812

(22) Filed: Aug. 13, 1999

(51) Int. Cl.⁷ .................... G01N 31/00; G06F 19/00; A01N 65/00; A61K 35/78
(52) U.S. Cl. .................... 702/23; 702/22; 702/30; 424/725
(58) Field of Search ................ 424/191.1, 725; 702/22, 23, 30

(56) References Cited

U.S. PATENT DOCUMENTS 4,774,229 A * 9/1988 Jordan .................... 514/25
5,607,693 A * 3/1997 Bonte et al. ............. 424/450

FOREIGN PATENT DOCUMENTS

JP  403190809 A * 8/1991 .............. 424/195.1

OTHER PUBLICATIONS

Gupta et al. Review On Phytochemical And Pharmacological Aspects Of Tribulus Terrerstris Linn Indian Drugs 34(B) pp. 422–424, Feb. 22, 1997.*

Hoffman, D. The Herbal Handbook pp. 201–211, 1987.*

* cited by examiner

Primary Examiner—Jon P. Weber
Assistant Examiner—Patricia Patton
(74) Attorney, Agent, or Firm—Cislo & Thomas LLP

(57) ABSTRACT

A cream made from the herb Tribulus Terrestris L. The cream preparation is made by low temperature water/alcohol extraction of Tribulus Terrestris L. After water/alcohol extraction of the herb Tribulus Terrestris L the extract is concentrated with a vacuum evaporator and mixed with a cream to concentrations of about 5, 10, 15% based on raw starting material. A number of factors are critical in preparation of the Tribulus Terrestris L raw material. These include: time of harvesting, part of the herb used, specific geographic area in Bulgaria where the herb is gathered, method of harvesting, and low temperature drying. Adherence to these factors guarantees high steroidal saponin, sapogenin and sterol content of the raw material used for making the cream. The finished cream has very strong anti-bacterial, anti-inflammation, anti-virus, anti-herpes effect and has been found to be highly useful in treating vulvo-vaginitis, vulvo-hemorrhoids, varicose veins and acne with. In some cases it blocks cancer cells from growing. This product was also found to be very successful in suppository form for the treatment of vulvo-vaginal, vulvo-hemorrhoidal and colonic conditions.

7 Claims, 5 Drawing Sheets

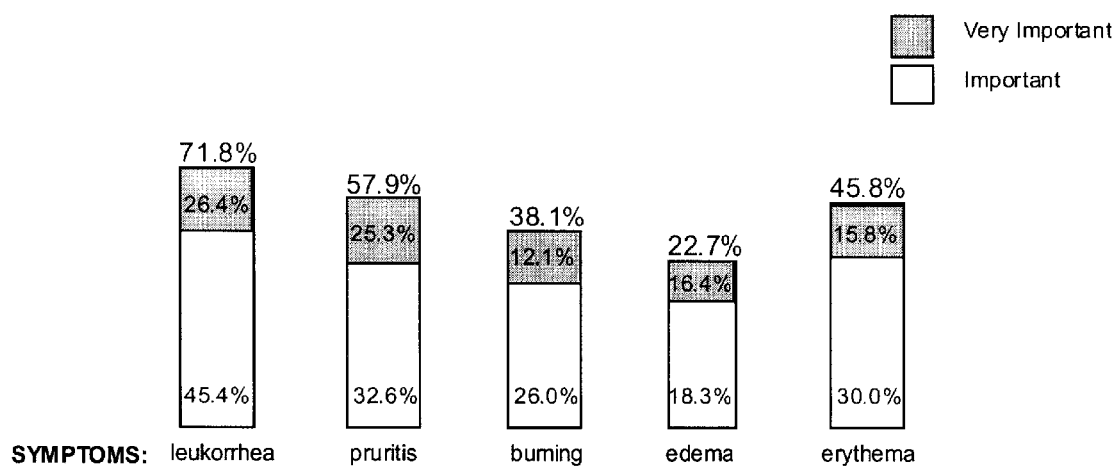
Figure 1. Complaint of vulvo-vaginitis symptoms evaluated by importance

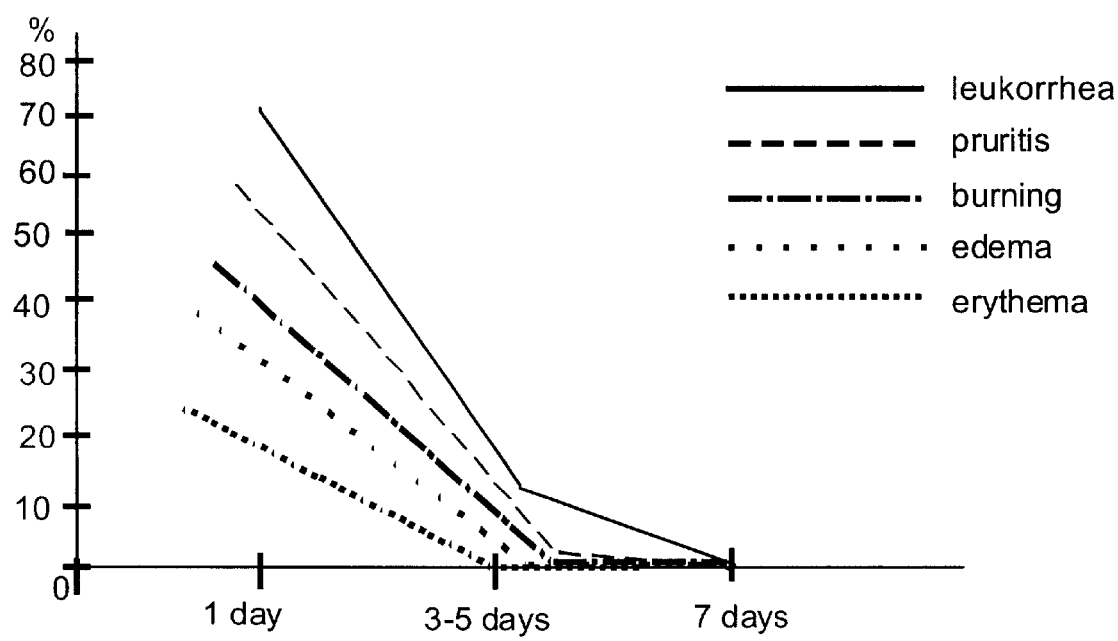
Figure 2. Evaluation of symptoms after first treatment

| SYMPTOMS | Day 1 % | Day 3-5 % | Day 7 % |
| --- | --- | --- | --- |
| Leukorrhea | 71.8 | 11.4 | 2.0 |
| Pruritis | 57.9 | 2.0 | 2.0 |
| Burning | 38.1 | 2.0 | 0 |
| Edema | 22.7 | 0.8 | 0 |
| Erythema | 45.8 | 4.1 | 2.0 |

Figure 3. Evaluation of symptoms after first treatment

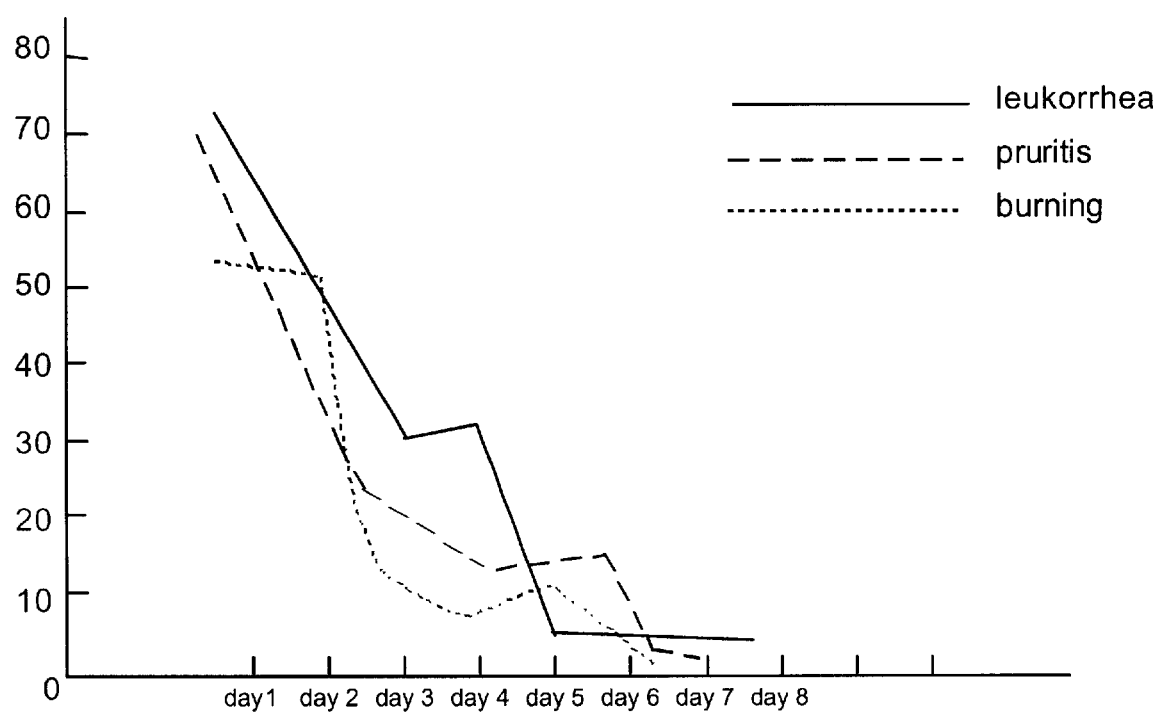
Figure 4. Daily patient evaluation of improvement of symptoms

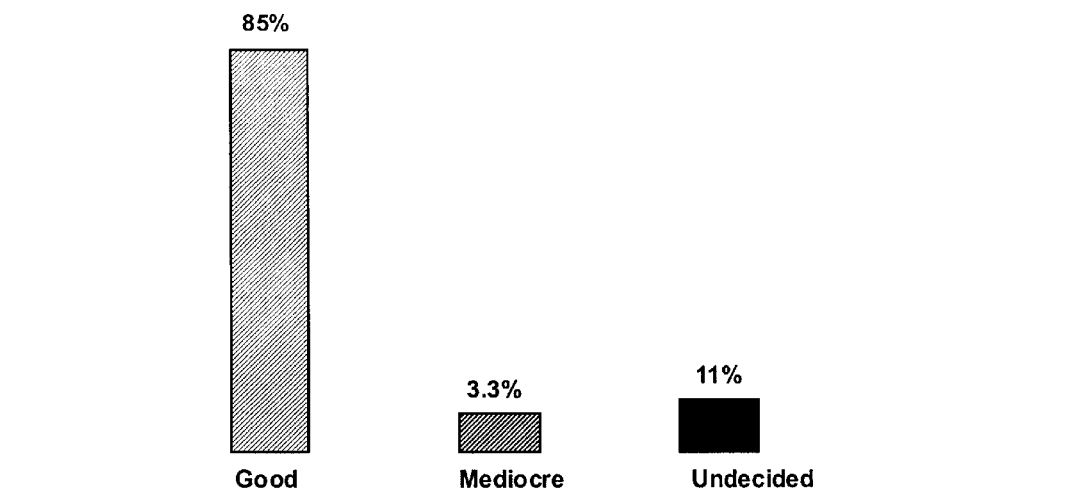
Figure 5. Physician assessment of results of treatmentt

METHOD FOR TESTING FOR READINESS FOR HARVESTING OF TRIBULUS TERRESTRIS L. HAVING HIGH STEROIDAL SAPONIN CONTENT

BACKGROUND OF THE INVENTION

The present invention relates to the field of therapeutic compounds for the treatment of diseases of the skin. In particular the present invention relates to creams made from the herb Tribulus Terrestris which are useful in the treatment of vulvo-vaginitis, vulvohemorrhoids, varicose veins and acne.

Tribulus Terrestris, commonly known as "Puncture Vine" or Caltrop fruit, is an herb that has been used for centuries in Europe for hormone insufficiency in men and women. It has also been used in the treatment of liver, kidney and urinary tract disease, and all types of skin disorders by Chinese herbalists for over 400 years.

In recent years Tribulus Terrestris has been touted as a dietary supplement for improving athletic performance. It has been discovered that ingestion of Tribulus Terrestris significantly elevates the level of several hormones: Testosterone; Luteinizing Hormone; Follicle Stimulating Hormone; and Estradiol. Clinical studies on Tribulus, conducted at the Chemical Pharmaceutical Institute in Sofia, Bulgaria, showed improved reproductive functions, including increased sperm production and Testosterone levels in men. Among women, Tribulus Terrestris increased the concentration of hormones including Estradiol, with Testosterone being very slightly influenced, thereby improving reproductive function, libido and ovulation. The active components of Tribulus Terrestris have a stimulating effect on the immune, sexual and reproductive systems, leading to improved muscle building, stamina and endurance. Other positive changes observed in a number of cases were a reduction in cholesterol, enhanced mood and well-being. No adverse effects to the central nervous or cardiovascular systems were noted in any of the clinical studies.

However, to date, no one has realized that a cream made from Tribulus Terrestris might have a very strong anti-bacterial, anti-inflammation, anti-virus, anti-herpes effect and be highly effective for treatment of vulvo-vaginitis, vulvo-hemorrhoids, varicose veins and acne.

Development of a cream made from Tribulus Terrestris which has a very strong anti-bacterial, anti-inflammation, anti-virus, anti-herpes effect represents a great improvement in the fields of dermatology and gynecology and satisfies a long felt need of dermatologists and gynecologists.

SUMMARY OF THE INVENTION

The present invention is a cream made from the herb Tribulus Terrestris L for topical use. It has very strong anti-bacterial, anti-inflammation, anti-virus, anti-herpes effect and has been found to be highly useful in treating vulvo-vaginitis, vulvo-hemorrhoids, varicose veins and acne with. In some cases it blocks cancer cells from growing.

The cream preparation is made by low temperature water/alcohol extraction of Tribulus Terrestris L. A number of factors are critical in preparation of the Tribulus Terrestris L raw material. These include: time of harvesting, part of the herb used, specific geographic area in Bulgaria where the herb is gathered, method of harvesting, and low temperature drying. Adherence to these factors guarantees high steroidal saponin, sapogenin and sterol content of the raw material used for making the cream.

After water/alcohol extraction of the herb Tribulus Terrestris L the extract is concentrated with a vacuum evaporator and mixed with a cream to concentrations of about 5, 10, 15% based on raw starting material. This product was also found to be very successful in suppository form for the treatment of vulvo-vaginal, vulvo-hemorrhoidal and colonic conditions.

An appreciation of the other aims and objectives of the present invention and an understanding of it may be achieved by referring to the accompanying drawings and description of a preferred embodiment.

BRIEF DESCRIPTION OF THE DRAWINGS

FIG. 1 is a graph showing the importance of vulvo-vaginitis symptoms.

FIG. 2 is a graph showing how various symptoms improve with treatment.

FIG. 3 is a chart of the data used in preparation of FIG. 2.

FIG. 4 is a graph showing improvement in various symptoms.

FIG. 5 is a bar chart showing physician assessment of results of treatment.

DETAILED DESCRIPTION OF THE PREFERRED EMBODIMENT

Method of Harvesting the Herb Tribulus Terrestris L

1. The herb Tribulus Terrestris L is harvested from the southern part of Bulgaria where high concentration of steroidal saponins, sapogenins and sterols in the herb has been confirmed by years of analysis.

2. The parts of the herb Tribulus Terrestris L used are: leaves, fruits and stems.

3. Method for quick analysis of steroidal saponins, sapogenins and sterols:

Take 500 mg. from the harvested and dried (at a temperature of 45° C.) plant material (leaves, fruits, and stems) of Tribulus Terrestris L.

Blend for 15 minutes in a blender with 200 ml. water. If the white foam level of the saponins is 1.5 times higher than the water level, the plant is ready for harvesting.

Once activity of steroidal saponins is confirmed, the harvesting process must be finished within one week.

Time of harvesting in Bulgaria is usually between July 1–July 30 and, depending on the weather conditions, as late as August 15.

4. Once the plant has been harvested it must be stored in a dry place or dried immediately.

5. Drying of the herb must be done at a low temperature (40° C.) in an oven or at room temperature in a dry, very well ventilated facility. In order to keep the activity of the steroidal saponins in the raw material high the moisture content has to be less than 10%.

Extraction Method of the Herb Tribulus Terrestris L

Extraction is done with a blender. Prior to blending, a high speed shredder and mixer pulverizes the tissues thereby completely releasing the steroidal saponins and sapogenins from the herb. The size of the cuts is 0.1 mm to 10 mm. A mixture of leaves, fruit and stems is used.

EXAMPLE

Shred a mixture of leaves, fruit and stems of Tribulus Terrestris to a size of 0.1 to 10 mm in a shredder. For each 1 g of mixture, add about 300 ml deionized (DI) water and extract for about 15 min in a blender. Sufficient speed should be used to create a substantial vortex. Add about 150 ml ethyl alcohol, mix, leave for 48 hours and then filter. Distill off the ethyl alcohol then concentrate the water extract with a vacuum evaporator to about 1 ml for each g of starting mixture. Finally, mix with a cream base to a concentration of 5% and 7.5% Tribulus Terrestris L concentrated water extract. Any cream base used for dermatological uses can be used. Alternatively, mix with glycerin or paraffin to make into a suppository form.

Testing of Creams

Creams made as described above with 5% and 7.5% Tribulus Terrestris L concentrated water extract were used for local treatment in 275 women with vulvo-vaginitis. A physician carried out the treatment after obtaining samples from the vagina, cervix and vulva. In most cases the condition was classified as candidiasis. Application of the creams was done after the confirmation of the diagnosis through microbiological testing. Quick improvement of the symptoms of the vulva was noted even on the first day of the application of the cream.

The treatment had very good acceptance according to the opinion of the patients as well as their physicians. Vaginal antiseptic creams are preparations for treatment of local problems of the vulva in the region of the vulvo-vagina. The epithelia of the vagina is an effective barrier against infection, however, at the same time it is a propitious environment for the development of protective flora and can permit development of numerous pathogenic microorganisms. These vaginal antiseptic creams are used for the treatment of vulvo-vaginitis through their action on the genital mucosa as a skin disinfectant.

Efficacy in addition to good acceptance in one delicate and inflamed area are the main qualities of the treatment. The creams are antiseptic against numerous microorganisms and do not irritate. Their action has a maximal effectiveness in pH 4–5.6, which is precisely the physiologic value of pH in the vagina as well as the pathological values of pH there.

For this reason a multi-parameter investigation was done with 275 women suffering clinically from vulvo-vaginitis, proven micro biologically, in order to determine the efficacy, lack of side effects and acceptance of the treatment for infections of the lower genitalia.

Patients: The investigation was conducted with women above 16 years of age with vulvo-vaginitis with various etiology (bacteria, fungi, parasites, etc.) with at least two of the following symptoms:

leukorrhea pruritus burning edema erythema

Patients with the associated symptoms of the upper genitalia were excluded from the study.

Two hundred and seventy-five (275) patients were followed for a period of 9 months. The patients' ages varied from 16 to 62 years with a mean age of 32. More than 90% were younger than 45 years. In 71.6% of the cases the patients were using contraception, most often oral (44.40%) and intra-uterine (25.1%).

Lower genital pathology (vulvo-vaginitis) was the cause for consultation in 63.3% of the cases and 29.1% were regular patients in whom vulvo-vaginitis was diagnosed. A tendency of recurrence is seen in approximately 40.7% of women diagnosed with vulvo-vaginitis.

The initial diagnosis during investigation was:

candidiasis—83.9% trichomonasis—7.3% bacterial vaginosis—4.0% chlamidia cervicitis—0.8% herpes—0.8% e-coli—0.8% condyloma—0.8% infected ectopia—0.8% abscess of the left labia—0.8% diagnosis of mycosis was confirmed in 76% of the cases and rejected in 24%.

The treatment with the antiseptic creams was carried out by a physician, who used the following technique of endocervical treatment:

With a speculum open the vagina. With swab, dry out and clean with the disinfecting solution. After that with a cotton swab, apply the cream of this invention to the whole vagina, including the cervix. After removing the speculum, apply cream also to the vulva. The treatment is not affected by the menstrual cycle.

Note: vaginal antiseptic creams will not replace etiologic treatment of the diseases of the vagina: they were applied in combination with the etiologic treatment. Creams were applied in combination with:

antimycotic locally—34% antimycotic general application in combination with local application—7% polyvalent wide spectrum local therapy—33% trichomonadicide, general application—13% oral antibiotics—3% anti-virus—1%

Investigation consisted of three obligatory check-ups. The first check-up was done at the beginning of treatment (first day of the check-up)thorough clinical gynecologic check-up, obligatory microbiological investigation and competent endocervical sampling. The second check up (second endocervical sample) was carried out on the seventh day. The third check-up was done on the fourteenth day of the treatment. In cases of regression, without complete healing on the fourteenth day, a new application of the cream to the vagina was done.

The total effectiveness of the treatment was evaluated on the basis of the development of the clinical symptoms, which motivated the person to be included in the investigation: leukorrhea, pruritus, burning, edema and erythema. Each clinical symptom was evaluated on a degree from 0 to 3, according to the intensity during each check-up:

0—lack

1—of low importance

2—important

3—very important

The following of all symptoms during the check-up allowed following the clinical development of the process.

Each undesirable effect was noted on the evaluation sheet. It was presented during the second check-up. The sheet required the patient to evaluate the acceptance of the treatment as well as the development of the symptoms, general treatment and the vaginal cream in particular.

Two clinical symptoms are the main complaint during vulvo-vaginitis—leukorrhea and pruritus (FIG. 1). During the etiological treatment and the treatment with the 7.5% cream, most of the important symptoms (No. 2 and 3) disappeared on the second check-up on day 7 of the treatment (FIGS. 2 and 3). Results were evaluated on day 3, day 5 and day 7. These results were very significant. In 93% of the cases the patients were considered healed. That is the total result is less or equal on day 3, 5 and 7.

Development of the symptoms was evaluated each day by the patient up to the 7$^{th}$ day of the treatment, which allowed for assessment of the speed of improvement of the leukorrhea, pruritus and burning. Symptoms of the leukorrhea, pruritus and burning had almost disappeared by the 3$^{rd}$–4$^{th}$ day. See FIG. 4.

Vaginal creams with 5% and 7.5% Tribulus Terrestris L were very well accepted by 9 out of 10 patients. Acceptance was perceived as good in 85% of the cases and mediocre in 3.3% (FIG. 5). Subjectively, acceptance was considered good by 98.4% of the patients and bad by 2.4%. Thus, treatment continues in 98% of the cases.

Side effects reported were:

itching slight irritation in the beginning slight redness in the beginning

Overall vaginal creams could be considered well received in practice treatment. Again it was not the objective of this investigation to have the 7.5% cream replace treatment, but to use it in combination with etiologic treatment: i.e. antimycotic or polyvalent, local or general. In other words, the 7.5% cream is not used as the main treatment for diseases of the vagina but as an additional treatment with a dual role. Use of the creams results in: faster action on the functional symptoms (pruritus, burning, pain), local treatment against inflammation and infection of the vulva. The only inconvenience is that the treatment and endocervical sample should be carried out by a gynecologist, well qualified to treat the inflammatory diseases of women. Thus, local treatment is recommended.

In this study the qualities of the 7.5% cream were as follows:

efficacy—in 70% of the patients the leukorrhea was diminished and in 93% was considered healed by the 7$^{th}$ day.

fast action, improvement of the functional symptoms even on the 3$^{rd}$ day.

acceptance—good in 87.7% of cases lack of side effects during application in 98% of cases.

The use of the 7.5% cream was pleasurable to most of the patients (endocervical sample only once, rarely second time, by physician) and better than formerly used antiseptics in 39.6% of cases, where there was a former practice of application of antiseptic solutions and/or globules.

Two hundred and seventy-five (275) women with vulvo-vaginitis were treated with the 7.5% and 5% creams of this invention in combination with local or general treatment of the vagina. Most of the symptoms disappeared on the 3$^{rd}$–5$^{th}$ day or on the 7$^{th}$ day. During this study the treatment of vulvo-vaginitis passed through two phases: adapted etiologic treatment, and additional local treatment of the vulva, which decreases the functional symptoms and benefits fight against infection.

Vaginal antiseptic creams in 7.5% and 5% strength with their efficacy, acceptance and lack of side effects represent an additional local adapted treatment. This investigation was carried out in French Department Specialise Gynecologie Obstetrique Sofia, Bulgaria by Dr. B. Kirtchev.

The invention has been described with reference to particular embodiments. Other modifications and enhancements can be made without departing from the spirit and scope of the claims that follow.

What is claimed is:

1. A method for testing for readiness of harvesting of Tribulus terrestris L. comprising:

a. mixing an approximately 500 mg sample of Tribulus terrestris L. with approximately 200 ml of deionized water to create a mixture;

b. bending the mixture for about fifteen minutes in a container with sufficient speed to create a vortex;

c. immediately examining the level of foam and water in the container, and d. if there is at least 1.5 times as much foam as water, harvesting the entire crop of Tribulus Terrestris L. within the week, otherwise repeating steps (a) through (d) until there is at least 1.5 times as much foam as water.

2. The method of claim 1, wherein the sample of Tribulus terrestris L. consists essentially of leaves, fruits and stems.

3. A method of testing for readiness of harvesting of Tribulus terrestris L. comprising the steps of:

a. collecting a 500 mg sample of leaves fruit and stems of Tribulus terrestris L.;

b. adding about 200 ml deionized water;

c. blending for about 15 minutes in a blender with sufficient speed to create a substantial vortex;

d. immediately examining the level of foam and water in the blender; and e. if there is at least 1.5 times as much foam as water, harvesting the entire crop of Tribulus Terrestris L within the week, otherwise repeating steps a. through e. until there is at least 1.5 times as much foam as water.

4. The method of claim 3 wherein the sample of Tribulus Terrestris L. leaves, fruits and stems is dried at approximately 45° C. prior to performing step (a).

5. The method of claim 3 wherein the Tribulus Terrestris L. is harvested from southern Bulgaria.

6. The method of claim 3 wherein the Tribulus Terrestris L is harvested from southern Bulgaria between approximately July first and August 15.

7. The method of claim 6 wherein the Tribulus Terrestris L is harvested from southern Bulgaria between approximately July first and July thirtieth.

* * * * *